US012788622B2

(12) United States Patent
Long

(10) Patent No.: US 12,788,622 B2
(45) Date of Patent: Nov. 10, 2026

(54) CRYOGENIC PHYSICAL THERAPY CABIN AND CRYOGENIC PHYSICAL THERAPY CABIN SYSTEM

(71) Applicant: Zhigang Long, Beijing (CN)

(72) Inventor: Zhigang Long, Beijing (CN)

( * ) Notice: Subject to any disclaimer, the term of this patent is extended or adjusted under 35 U.S.C. 154(b) by 555 days.

(21) Appl. No.: 18/449,522

(22) Filed: Aug. 14, 2023

(65) Prior Publication Data

US 2024/0050271 A1 Feb. 15, 2024

(30) Foreign Application Priority Data

Aug. 15, 2022 (CN) ......................... 202210974146.0

(51) Int. Cl.
*A61F 7/00* (2006.01)

(52) U.S. Cl.
CPC ............ *A61F 7/0053* (2013.01); *A61F 7/007* (2013.01); *A61F 7/0085* (2013.01); *A61F 2007/0086* (2013.01); *A61F 2007/0093* (2013.01)

(58) Field of Classification Search
CPC ...... A61F 7/0053; A61F 7/007; A61F 7/0085; A61F 2007/0086; A61F 2007/0093;
(Continued)

(56) References Cited

U.S. PATENT DOCUMENTS 4,044,772 A * 8/1977 Schloss .................. A61H 33/06 4/524
9,744,098 B2 * 8/2017 O'Keeffe ............. A61H 33/066
(Continued)

FOREIGN PATENT DOCUMENTS

CN 2461537 11/2001
CN 202751228 U * 2/2013
(Continued)

OTHER PUBLICATIONS

Office Action issued in Corresponding Chinese Application No. 202210974146.0, dated Mar. 19, 2024 (English Translation provided).

(Continued)

*Primary Examiner* — Joanne M Rodden
*Assistant Examiner* — Casey George Cha
(74) *Attorney, Agent, or Firm* — NORTON ROSE FULBRIGHT US LLP

(57) ABSTRACT

Embodiments of the present application disclose a cryogenic physical therapy cabin and a cryogenic physical therapy cabin system. The cryogenic physical therapy cabin includes: a cabin body; a cabin door, which is hinged with the cabin body to form at least one sauna room; a refrigeration module, which comprises an evaporator arranged on an inner wall of the cabin body; an air outlet module, which is arranged on the cabin body and includes fan blades and a fan electrically connected to the fan blades, wherein the fan is configured to drive the fan blades to rotate to generate a circulating airflow inside the sauna room; and a main control module, which includes a controller electrically connected to the fan and the refrigeration module, wherein the controller is configured to receive a user adjustment instruction and adjust operation states of the air outlet module and the refrigeration module according to the user adjustment instruction. With the cryogenic physical therapy cabin in embodiments on the present application, the operation state can be adjusted according to the user adjustment instruction, and thereby improving the intelligence level of the cryogenic physical therapy cabin.

9 Claims, 5 Drawing Sheets

(58) Field of Classification Search

CPC ...... A61F 2007/0094; A61F 2007/0057; A61F 2007/0095; A61F 2007/0096; A61H 33/005; A61H 33/6068; A61H 2033/0058; A61H 33/0095; A61H 35/00; A61H 2033/0079; A61H 33/063; A61H 2033/062; A61H 2035/004; A61H 2201/5038; A61H 2201/0184; A61H 2201/0214; A61H 2201/0221; A61H 2201/0242; A61H 2201/025; A61H 2201/0264; A61H 2201/5007; A61H 2201/501; A61H 2201/5082; A61H 2201/5097; A61H 33/066; Y02B 30/70; F25B 2600/2525

See application file for complete search history.

(56) References Cited

U.S. PATENT DOCUMENTS

| | | | | |
|---|---|---|---|---|
| 10,905,584 | B2 * | 2/2021 | Trembley | A61F 7/0053 |
| 2013/0025302 | A1 | 1/2013 | Lyubchenko | |
| 2016/0089262 | A1 * | 3/2016 | Kuehne | A61F 7/0053<br>606/20 |

FOREIGN PATENT DOCUMENTS

| | | | | |
|---|---|---|---|---|
| CN | 104188791 | | 12/2014 | |
| CN | 204004641 | | 12/2014 | |
| CN | 204158701 | | 2/2015 | |
| CN | 105877992 | A | 8/2016 | |
| CN | 107928864 | | 4/2018 | |
| CN | 105877992 | B | 10/2018 | |
| CN | 210423929 | | 4/2020 | |
| CN | 112780815 | | 5/2021 | |
| EP | 3628280 | A1 * | 4/2020 | A61F 7/0085 |
| JP | 2011045556 | | 3/2011 | |
| KR | 200360491 | Y1 * | 8/2004 | A61H 33/066 |
| KR | 20200069816 | | 6/2020 | |
| WO | WO-2017023958 | A1 * | 2/2017 | F25B 49/022 |

OTHER PUBLICATIONS

*Refrigerator Repair from Beginner to Mastery*, edited by Pengfei Chen, 3rd ed., National Defense Industry Press, 2011, Beijing, p. 84 (English Translation of relevant parts provided).

Extended European Search Report issued in corresponding European Application No. 23191319.5, dated Jan. 2, 2024.

* cited by examiner

CRYOGENIC PHYSICAL THERAPY CABIN AND CRYOGENIC PHYSICAL THERAPY CABIN SYSTEM

CROSS-REFERENCE TO RELATED APPLICATION

The present application claims the benefit of priority to Chinese Patent Application No. 202210974146.0, filed on Aug. 15, 2022, the entire contents of which are hereby incorporated by reference in their entirety.

TECHNICAL FIELD

The present application relates to cryogenic sauna physical therapy technology, and in particular to a cryogenic physical therapy cabin and a cryogenic physical therapy cabin system.

BACKGROUND

Cryogenic physical therapy, also known as cryogenic sauna, means that a human body enters an extremely low temperature environment and maintains for 2-3 minutes, after cryogenic freezing stimulates skins, the body releases endorphins, thereby enabling the body to accelerate blood circulation, continuously burn fat, increase skin elasticity, restore from muscle fatigue and achieve other functions and effects. A cryogenic physical therapy device such as a cryogenic physical therapy cabin refers to a refrigeration device with a extremely low temperature for providing physical therapy for the human body. In related technologies, the cryogenic physical therapy cabin cannot adjust the operation state thereof according to a user adjustment instruction, and the intelligence level thereof is relatively low.

SUMMARY

Embodiments of the present application provides a cryogenic physical therapy cabin and a cryogenic physical therapy cabin system, which can adjust operation states thereof according to a user adjustment instruction and improve the intelligence level thereof. The specific technical solution is as follows:

An embodiment in a first aspect of the application provides a cryogenic physical therapy cabin, which includes: a cabin body; a cabin door, which is hinged with the cabin body to form at least one sauna room; a refrigeration module, which includes an evaporator arranged on an inner wall of the cabin body; an air outlet module, which is arranged on the cabin body and includes fan blades and a fan electrically connected to the fan blades, wherein the fan is configured to drive the fan blades to rotate to generate a circulating airflow inside the sauna room; and a main control module, which includes a controller electrically connected to the fan and the refrigeration module, wherein the controller is configured to receive a user adjustment instruction and adjust operation states of the air outlet module and the refrigeration module according to the user adjustment instruction.

In the cryogenic physical therapy cabin provided in the embodiments of the application, the refrigeration module, the air outlet module, and the main control module are integrated on the cabin body. The refrigeration module can cool a sauna room in the cryogenic physical therapy cabin to form an extremely low temperature environment that can be used for single or multiple people for physical therapy. During the use of the cryogenic physical therapy cabin, the main control module can adjust operation states of the refrigeration module and the air outlet module connected to the main control module according to a user adjustment instruction. The user adjustment instruction includes a physical therapy temperature, a physical therapy wind speed, physical therapy time, etc. set according to the user's personal preferences and tolerance, so that the temperature and the air volume inside the sauna room are more suitable for the user's needs. In addition, after users enters the sauna room for physical therapy, the main control module can further adjust the corresponding operation state according to different user adjustment instructions, further adapting to user needs. According to a specific user adjustment instruction, the main control module can adjust the temperature in the cryogenic physical therapy cabin to a state corresponding to this user adjustment instruction. The internal state of the cryogenic physical therapy cabin can be adjusted according to different user needs, which can increase the intelligence level of the cryogenic physical therapy cabin. Furthermore, the air outlet module is arranged in the cryogenic physical therapy cabin, so that the cooling in the sauna room is more comprehensive, fast and more uniform, which is conducive to rapid cooling of the sauna room and shortening the waiting time of the user.

In addition, a cryogenic physical therapy cabin according to embodiments of the present application may also have the following additional technical features.

In some embodiments of the application, the cryogenic physical therapy cabin further includes a first heater, which is arranged on the evaporator and is electrically connected to the controller, wherein the controller is further configured to adjust an operation state of the first heater.

In some embodiments of the application, the cryogenic physical therapy cabin further includes a first temperature sensor, which is arranged on the inner wall of the cabin body, wherein first temperature sensor is electrically connected to the controller, and is configured to send a detected first temperature value to the controller; and the controller is further configured to adjust a rotation speed of the fan according to the first temperature value and the user adjustment instruction.

In some embodiments of the application, the user adjustment instruction includes a preset target apparent temperature, and the controller being further configured to adjust the rotation speed of the fan according to the first temperature value and the user adjustment instruction, includes: the controller being further configured to obtain a current first rotation speed of the fan, and calculate a current actual apparent temperature according to the first rotation speed and the first temperature value, the controller being further configured to calculate a difference value between the actual apparent temperature and the target apparent temperature, and adjust the rotation speed of the fan to a second rotation speed according to the difference value.

In some embodiments of the application, the cabin body further includes a cover plate connected to the inner wall of the cabin body, and an air duct is formed between the cover plate and the inner wall, wherein the evaporator is arranged at a first end of the air duct, and the fan blades are arranged at a second end of the air duct, and the cover plate includes an air outlet connected to the second end, and a return air inlet connected to the first end.

In some embodiments of the application, the cryogenic physical therapy cabin further includes a human body sensor and a timer, which are electrically connected to the controller, wherein the human body sensor is arranged in the sauna room, and the controller is further configured to control the timer on or off according to a sensing result of the human body sensor; and the controller is further configured to control the operation states of the air outlet module and the refrigeration module according to a timing duration of the timer.

In some embodiments of the application, the cabin door further includes a glass window structure, which includes at least two pieces of glass fixedly connected and arranged in parallel with each other, wherein there is an air gap between adjacent two pieces of glass, and an electric heater is arranged on a first glass in the at least two pieces of glass close to the sauna room; and the controller is electrically connected to the electric heater, and is configured to control an operation state of the electric heater.

In some embodiments of the application, the cryogenic physical therapy cabin further includes a main control operation panel, which is arranged on an outer wall of the cabin body and is electrically connected to the controller, wherein the main control operation panel is configured to receive the user adjustment instruction and send the user adjustment instruction to the controller.

In some embodiments of the application, the main control operation panel includes a central control module, a data acquisition module, a communication module, and a storage module, wherein the main control operation panel is electrically connected to the controller.

In some embodiments of the application, at least one air pressure balance hole is arranged in the cabin body, and connects an interior and an exterior of the cabin body; and at least one air pressure balance valve is arranged in each of the at least one air pressure balance hole, and includes a support and an elastic sheet, wherein the support is abutted against a hole wall of the air pressure balance hole, and at least one through hole is arranged in the support; the elastic sheet is connected to the support, and along an axis direction of the air pressure balance hole, the elastic sheet covers the at least one through hole, and the elastic sheet is movable along a direction close to or away from the support.

In some embodiments of the application, the refrigeration module includes a compressor refrigeration structure or a liquid nitrogen refrigeration structure.

An embodiment in a second aspect of the application provides a cryogenic physical therapy cabin system, which includes a mobile terminal and the cryogenic physical therapy cabin according to any embodiment in the first aspect mentioned above, wherein the mobile terminal is communicated with the main control module of the cryogenic physical therapy cabin through signals.

BRIEF DESCRIPTION OF THE DRAWINGS

In order to more clearly describe the technical solution of the embodiments of the application or of the prior art, drawings needed in the embodiments and the prior art will be briefly described below. Obviously, the drawings described below are for only some embodiments of the present application, one of ordinary skills in the art can also obtain other embodiments on the basis of these drawings.

REFERENCE NUMBERS

Figure 1:
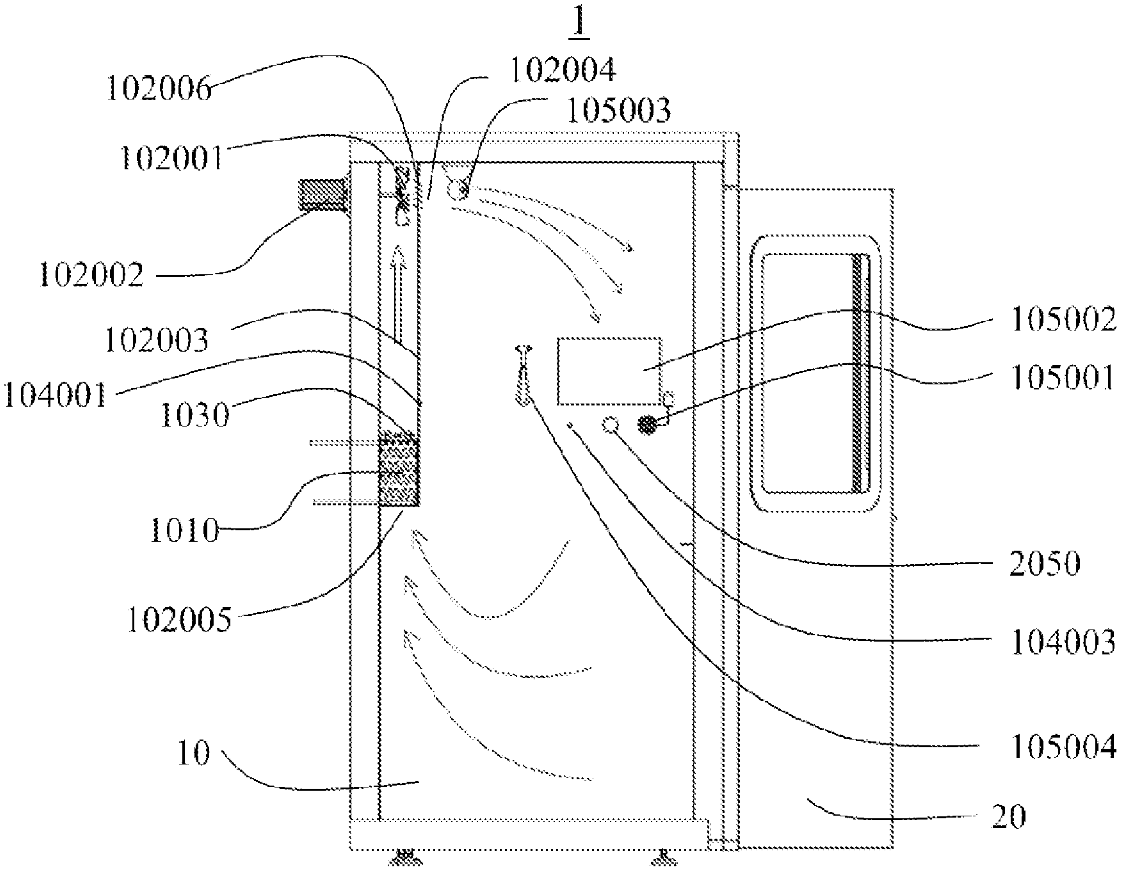
FIG. 1 is a schematic structural diagram illustrating the interior of a cryogenic physical therapy cabin provided in the embodiments of the application.

Cryogenic physical therapy cabin 1; Cabin body 10; Evaporator 1010; Fan blade 102001, Fan 102002, Cover plate 102003, Air outlet 102004, Return air inlet 102005, Wind guide plate 102006; First heater 1030; First temperature sensor 104001, limit switch 104002, Human body sensor 104003; Intercom system 105001, Display screen 105002, Camera 105003, Emergency glass hammer 105004; Air pressure balance hole 106001, Air pressure balance valve 106002, Second support 106003, Elastic sheet 106004, Through hole 106005, Pressing sheet 106006, Bracket 106007;

Cabin door 20; Door closer 2010; Sealing strip 2020; Door lock structure 2030, Lock body portion 203001, Lock shaft portion 203002, fixed part 203003, Slider 203004, First support 203005, Electromagnet 203006, Connecting plate 203007, Bent hook portion 203008, Suction plate portion 203009, First receiving slot 203010, First mounting plate 203011, First side plate 203012, First guide rail 203013, First pulley 203014, Second side plate 203015, Second guide rail 203016, Second pulley 203017, Second mounting plate 203018, First elastic element 203019; Driving structure 2040, Gear 204001, Gear rack 204002, Electric motor 204003; Emergency switch 2050, Connector 205001, Eccentric wheel 205002, Microswitch 205003; Glass window structure 2060, First glass 206001, Second glass 206002, Electric conductor 206003; Main control operation panel 3010.

DETAILED DESCRIPTION

In order to more clearly describe the technical solution of the embodiments of the application or of the prior art, drawings needed in the embodiments and the prior art will be briefly described below. Obviously, the drawings described below are for only some embodiments of the present application, one of ordinary skills in the art can also obtain other embodiments on the basis of these drawings.

For ease of description, spatial relative relationship terms may be used in the description to describe the relationship of an element or a feature to another element or another feature as shown in the figures, such as "interior," "exterior," "rear", "top", "bottom", "below", "under", "above", "over", etc. These spatial relative relationship terms mean to include different orientations of devices in use or operation, except for those depicted in the drawings.

The technical solution of the embodiments of the application will be clearly and fully described in detail with reference to the drawings of the embodiments of the present application. Obviously, the embodiments described herein are only some instead of all of the embodiments of the present application. Based on the embodiments the application, all other embodiments obtained by those of ordinary skills in the art based on the application are within the scope of the present application.

Figure 2:
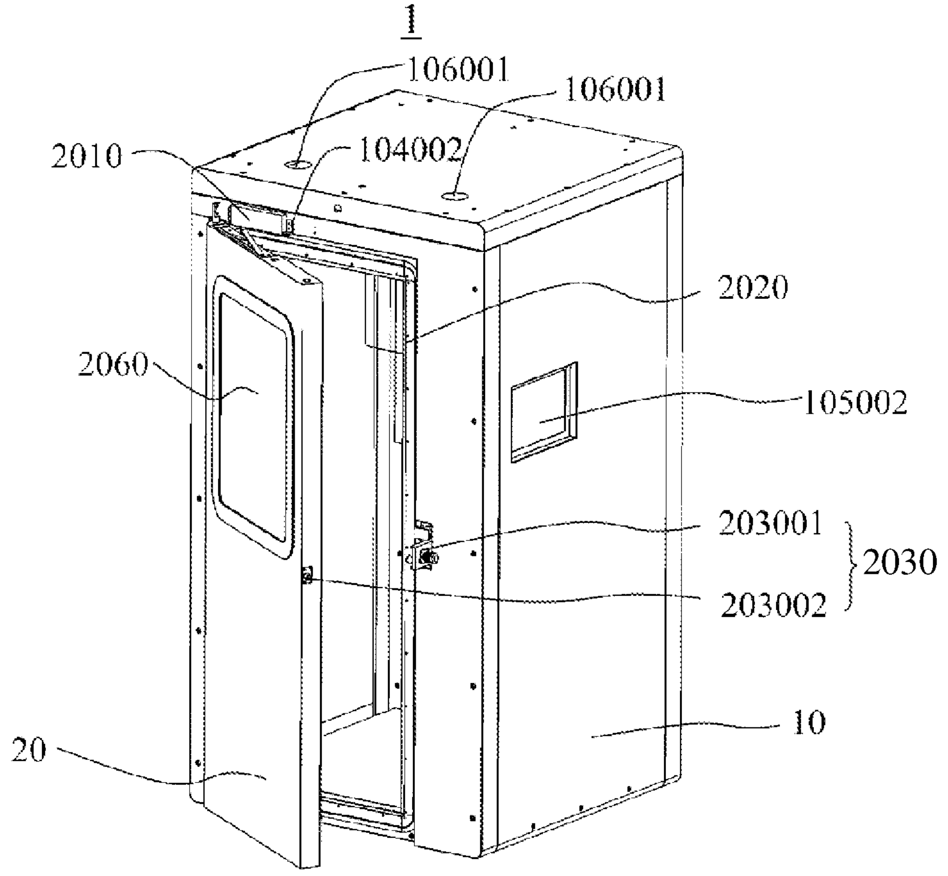
FIG. 2 is a schematic structural diagram of the cryogenic physical therapy cabin provided in the embodiments of the application.

In embodiments in the first aspect of the application, a cryogenic physical therapy cabin 1 is provided, as shown in FIGS. 1 and 2. The cryogenic physical therapy cabin 1 includes: a cabin body 10; a cabin door 20, which is hinged with the cabin body 10 to form at least one sauna room; a refrigeration module, which includes an evaporator 1010 arranged on an inner wall of the cabin body 10; an air outlet module, which is arranged on the cabin body 10 and includes fan blades 102001 and a fan 102002 electrically connected to the fan blades 102001, wherein the fan 102002 is configured to drive a rotation of the fan blades 102001 to generate a circulating airflow inside the sauna room; and a main control module, which includes a controller electrically connected to the fan 102002 and the refrigeration module, wherein the controller is configured to receive a user adjustment instruction and adjust operation states of the air outlet module and the refrigeration module according to the user adjustment instruction.

After connecting the cabin body 10 and the cabin door 20, the cabin has a substantially rectangular overall shape. Preferably, surface layers of the cabin body 10 and the cabin door 20 are made of a metal plate. Optionally, a plurality of thermal insulation layers can be arranged between inner layers and outer layers of the cabin body 10 and the cabin door 20. The thermal insulation layers are made of a material with a lower thermal conductivity, such as a polyurethane foam material or a vacuum insulation plate, and thus the sealing and insulation of the sauna room can be increased. Optionally, as shown in FIG. 1, the bottom of the cabin body 10 is arranged with casters to facilitate movement. The shape of the cryogenic physical therapy cabin is not limited in the application. For example, the cabin body 10 and the cabin door 20 can be enclosed in a cube, a cylinder, an irregular polyhedron, or an egg shape.

The refrigeration module is configured to cool the air in the sauna room. Specifically, the refrigeration module can maintain the sauna room at a low temperature through the evaporation and the compression of a circulating refrigerant. The evaporator 1010 is arranged on the inner wall of the cabin body 10. the refrigerant absorbs a large amount of heat during the evaporation of the evaporator 1010 to achieve cooling of the air in the sauna room. When the cryogenic physical therapy cabin includes one sauna room, the temperature range of the sauna room can be −60° C. to −190° C.

Optionally, the refrigeration module can also include a compressor, a condenser and an expansion valve, etc., so that the evaporation and compression of the refrigerant are carried out circularly. The compressor, the condenser, and the expansion valve are arranged on an outer wall of the cabin body 10. The airflow generated by the air outlet module can produce a forced convection of the air in the sauna room, and generate a heat exchange with the cold air close to the evaporator 1010, so that the temperature in the sauna room is distributed more evenly. Preferably, as shown in FIG. 1, the fan blades 102001 are arranged inside the cabin body 10, and the fan 102002 is arranged outside the cabin body 10, which can reduce the probability that the fan 102002 cannot be activated again due to an extremely low temperature inside the cabin body 10, and is convenient for extending the continuous operation time of the fan 102002.

The main control module can be an assembly in which hardware such as a processor, a memory, etc. is integrated. The main control module can independently perform functions such as a data storage, a signaling interaction and a processing function on the operation parameters of the refrigeration module and the air outlet module, so as to control the refrigeration module and the air outlet module.

The user adjustment instruction can be input through an input component integrated into the main control module. The user adjustment instruction can also be input through terminals such as mobile phones and remote controllers that establish communication connections with the main control module, wherein, the input component can be a physical switch, a button, a touchpad, etc. The input component can be set according to the application scenario of the cryogenic physical therapy cabin, and is not limited in this application. The user adjustment instruction include setting the physical therapy temperature, physical therapy wind speed, and physical therapy time according to the user's personal needs.

In the cryogenic physical therapy cabin 1 provided in the embodiment of this application, the cabin body 10 is integrated with a refrigeration module, an air outlet module, and a main control module. The refrigeration module can cool the sauna room in the cryogenic physical therapy cabin 1 to form an extremely low temperature environment that can be used for single or multiple people for physical therapy. During the use of cryogenic physical therapy cabin 1, the main control module can adjust the operation states of the refrigeration module and the air outlet module connected to it according to the user adjustment instruction. The user adjustment instruction includes a physical therapy temperature, a physical therapy wind speed, physical therapy time, etc. set according to the user's personal preferences and tolerance, to make the temperature and air volume inside the sauna room more suitable for the user's needs. In addition, after users enter the sauna room for physical therapy, the main control module can further adjust the corresponding operation state according to different user adjustment instructions, further adapting to user needs. According to a specific user adjustment instruction, the main control module can adjust the temperature in the cryogenic physical therapy cabin 1 to a state corresponding to this user adjustment instruction. The internal state of the cryogenic physical therapy cabin 1 can be adjusted according to different user needs, which can increase the intelligence level of the cryogenic physical therapy cabin 1. In addition, the air outlet module is arranged in the cryogenic physical therapy cabin 1, so that cooling in the sauna room is more comprehensive, faster, and more uniform, which is conducive to rapid cooling of the sauna room and shortening the waiting time of the user.

In some embodiments of the present application, as shown in FIG. 1, the cryogenic physical therapy cabin 1 further includes a first heater 1030, which is arranged on the evaporator 1010 and electrically connected to the controller, and the controller is further configured to adjust the operation state of the first heater 1030.

The first heater 1030 generates heat after being powered on, causing the frost on the surface of the evaporator 1010 to melt. In the embodiment of this application, defrosting treatment is performed on the evaporator 1010 by fixing the first heater 1030 on the evaporator 1010, thereby reducing the probability that the cooling effect of the evaporator 1010 is reduced due to frost formed on the surface.

The power on and off of the first heater 1030 are controlled by the controller. Specifically, the controller can start or stop the first heater 1030 at a fixed time. Optionally, within a heating cycle, the heating duration of the first heater can be 4 to 6 minutes to improve the defrosting effect of the first heater.

Optionally, while the first heater 1030 is activated, the controller can issue an instruction to shut down the fan 102002, stopping the rotation of the fan blades 102001 and reducing the energy consumption of the cryogenic physical therapy cabin 1.

The first heater 1030 can be located below the evaporator 1010 or inside the evaporator 1010. For example, the evaporator 1010 can include multiple fins and evaporation tubes arranged in the fins. The first heater 1030 can include a straight tube heater and a bent tube heater. The first heater 1030 in a straight tube shape is inserted into the fin through hole 106005 of the evaporator 1010, and the first heater 1030 in a bent tube shape is wound around the fin through hole 106005 of the evaporator 1010. The shape of the first heater 1030 or its fixed position on the evaporator 1010 are not limited in this application.

In other embodiments, the heating and defrosting treatment of the evaporator 1010 can also be achieved by transporting the high-temperature refrigerant in the compressor to the evaporator 1010. The specific process will not be repeated here.

In some embodiments of the present application, as shown in FIG. 1, the cryogenic physical therapy cabin 1 further includes a first temperature sensor 104001, which is arranged on the inner wall of the cabin body 10, and is electrically connected to the controller and configured to send the detected first temperature value to the controller. The controller is further configured to adjust the rotation speed of the fan 102002 according to the first temperature value and the user adjustment instruction. The user adjustment instruction includes a target apparent temperature, a physical therapy temperature, a physical therapy wind speed, etc. required by the user.

Further, the user adjustment instruction includes a preset target apparent temperature, and the controller being further configured to adjust the rotation speed of the fan according to the first temperature value and the user adjustment instruction, includes: the controller being further configured to obtain the current first rotation speed of the fan, and calculate a current actual apparent temperature according to the first rotation speed and the first temperature value, the controller being further configured to calculate a difference value between the actual apparent temperature and the target apparent temperature, and adjust the rotation speed of the fan to the second rotation speed according to the difference value.

In the embodiment of the application, after receiving the user adjustment instruction, the controller determines the physical therapy wind speed corresponding to the target apparent temperature according to the target apparent temperature required by the user, and adjusts the rotation speed of the fan 102002 to the first rotation speed according to the physical therapy wind speed. The controller can also adjust the cooling capacity of the refrigeration module according to the user's desired physical therapy temperature and maintain it for the first preset duration. The first temperature sensor 104001 obtains the first temperature value in real-time in the sauna room and sends the first temperature value to the controller. The controller calculates the current actual apparent temperature according to the first temperature value and the first rotation speed, determines the preset target apparent temperature according to the physical therapy temperature and physical therapy wind speed, and obtains the difference value between the actual apparent temperature and the preset target apparent temperature, and then adjusts the rotation speed of the fan 102002 to the second rotation speed according to the above difference value. The actual apparent temperature is the apparent temperature actually felt by the user in the sauna room, and the preset target apparent temperature is the apparent temperature calculated by the controller according to the user adjustment instruction. The first preset duration, first rotation speed, and second rotation speed can be set according to actual needs, such as the powers of the refrigeration module and the fan, and the temperature of the interior of the cryogenic physical therapy cabin, which is not limited in this application.

The apparent temperature refers to the degree of cold and warm that the human body feels, which is converted into a corresponding temperature. The apparent temperature will be comprehensively affected by the air temperature, wind speed and relative humidity. The relative humidity in the cryogenic physical therapy cabin 1 is kept in a relatively stable range, and the influence of the relative humidity on the apparent temperature is negligible. The contrast relationship among the wind speed, air temperature and apparent temperature in the cryogenic physical therapy cabin 1 is shown in Table 1, wherein, the wind speed can be the rotation speed of the fan. According to Table 1, the higher the wind speed, the lower the apparent temperature. For example, the air temperature in the cryogenic physical therapy cabin 1 is −100° C., and the apparent temperature of −120° C. can be reached when the wind speed is controlled at 2 m/s.

TABLE 1

| Apparent temperature ° C. | | Air temperature ° C. | | | | | | | | |
|---|---|---|---|---|---|---|---|---|---|---|
| | | 4 | −4 | −12 | −20 | −40 | −60 | −80 | −100 | −120 |
| Wind speed m/s | 1 | 3 | −5 | −14 | −23 | −44 | −68 | −90 | −110 | −132 |
| | 2 | 2 | −7 | −17 | −26 | −49 | −74 | −96 | −120 | −143 |
| | 4 | 1 | −9 | −20 | −29 | −54 | −79 | −103 | −129 | −153 |
| | 7 | 0 | −11 | −22 | −31 | −57 | −83 | −108 | −134 | −159 |
| | 9 | −1 | −12 | −23 | −33 | −59 | −86 | −111 | −138 | −164 |

During the process of using the cryogenic physical therapy cabin 1 for physical therapy, users will bring in a large amount of hot air when opening the door, and the human body will dissipate a lot of heat in the cryogenic physical therapy cabin 1, causing certain fluctuations in the temperature inside the sauna room. By adjusting the wind speed, the user's actual apparent temperature can be quickly changed, so that the actual apparent temperature can quickly reach the preset target apparent temperature, achieving the same effect of cryotherapy. Compared with the method of adjusting the refrigerating capacity of the refrigeration module, the method of adjusting the apparent temperature by changing the wind speed can greatly reduce the energy consumption, which is conducive to improving the effect of physical therapy.

When the controller determines that the temperature in the sauna room is high according to the first temperature value, the controller sends an instruction for increasing the rotation speed to the fan 102002, which increases the rotation speed of the fan 102002 and the wind speed in the sauna room, which is conducive to reducing the user's actual apparent temperature. On the contrary, when the controller determines that the temperature in the sauna room is low according to the first temperature value, the controller sends an instruction for reducing the rotation speed to the fan 102002, which reduces the rotation speed of the fan 102002 and the wind speed in the sauna room, which is conducive to increasing the user's actual apparent temperature.

During the physical therapy in the cryogenic physical therapy cabin 1, when the user's tolerance to the low temperature in the sauna room is low, the user can input a smaller physical therapy wind speed through the main control module, thereby reducing the wind speed in the sauna room and improving the user's actual apparent temperature. When the user's tolerance to the low temperature in the sauna room is high, the user can input a larger physical therapy wind speed through the main control module, thereby increasing the wind speed in the sauna room and reducing the user's actual apparent temperature.

The embodiment of this application achieves real-time adjustment of the temperature and air volume in the sauna room through the joint action of the first temperature sensor 104001 and the controller, further improving the intelligence level of the cryogenic physical therapy cabin 1 and bringing users a more comfortable user experience.

In other embodiments, the controller is further configured to adjust the first heater 1030 based on the first temperature value. The controller obtains the change rate of the first temperature value based on its variation over a certain period of time. When the change rate of the first temperature value is detected to be lower than a threshold, the controller controls the first heater 1030 to power on, thereby causing the evaporator 1010 to frost or melt ice.

In some embodiments of the application, as shown in FIG. 2, the cryogenic physical therapy cabin 1 further includes a door closer 2010 and a sealing strip 2020. One side of the door closer 2010 is fixedly connected with the cabin door 20, the other side of the door closer 2010 is fixedly connected with the cabin door 10, and the door closer 2010 is configured to drive the cabin door 20 to move in a direction close to the cabin door 10; the sealing strip 2020 is arranged around the surface edge at one side of the cabin door 20 towards the cabin body 10.

In the embodiment of the application, the door closer 2010 can drive the door 20 to rotate in a direction towards the cabin body 10, and the force exerted by the door closer 2010 on the cabin door 20 can make the cryogenic physical therapy cabin 1 drive the cabin door 20 to close without manual operations, thus greatly reducing the entry of air and water vapor, reducing frost in the cryogenic physical therapy cabin 1 and saving energy. The sealing strip 2020 is disposed between the cabin door 20 and the cabin body 10, playing a role of sealing and isolating the air flow between the interior and exterior of the cryogenic physical therapy cabin 1.

Optionally, the door closer 2010 can be a hydraulic device installed on the upper portion of the cabin door 20, which acts like a spring. When the cabin door 20 is opened, the door closer 2010 can automatically close the cabin door 20 by releasing the elastic energy after compression, which can ensure that the cabin door 20 is closed to the initial position accurately in time after opened.

Optionally, the sealing strip 2020 has multiple sealing lips arranged in parallel, all of which are closely abutted against the inner wall of the cabin body 10, thereby increasing the contact area between the sealing strip 2020 and the sealing structure between the cabin door 20 and the cabin body 10, allowing the sealing strip 2020 to fully contact the sealing structure, which is conducive to improving the sealing performance between the cabin door 20 and the cabin body 10.

Figure 3:
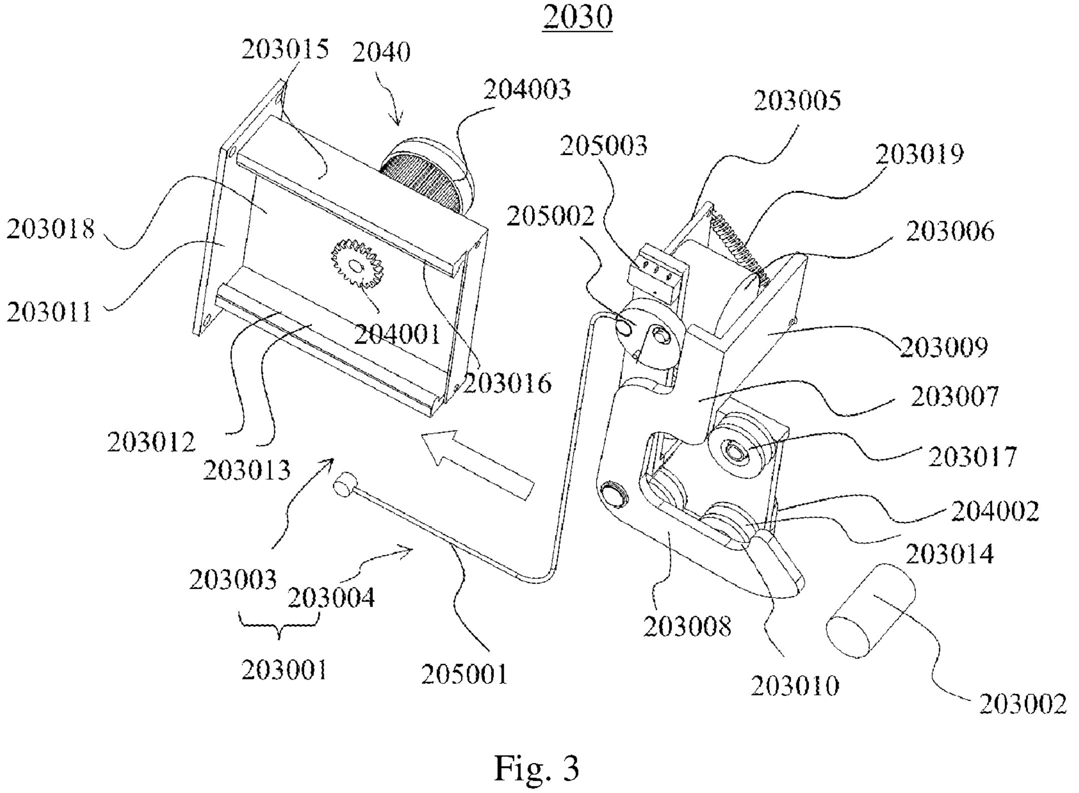
FIG. 3 is a schematic structural diagram of a door lock structure provided in the embodiments of the application.
Figure 4:
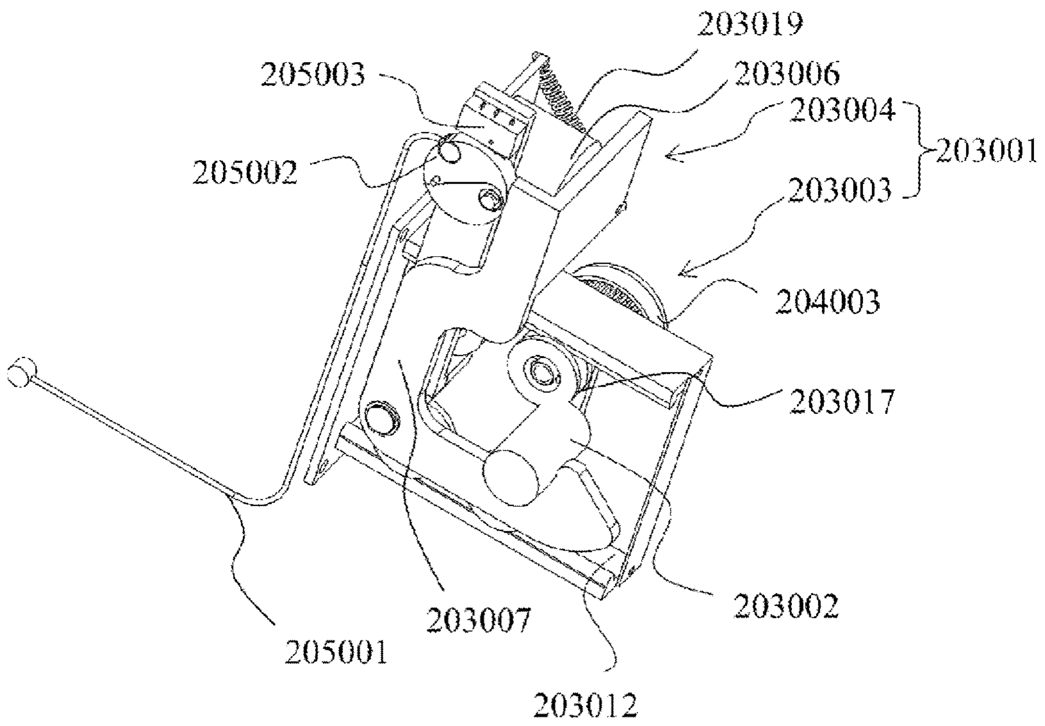
FIG. 4 is a schematic diagram illustrating the closed state of the door lock structure provided in the embodiments of the application.

In some embodiments of the present application, as shown in FIGS. 2 to 4, the cryogenic physical therapy cabin 1 further includes a door lock structure 2030, which includes a lock body portion 203001 and a lock shaft portion 203002. The lock body portion 203001 is arranged on the cabin body 10, and the lock shaft portion 203002 is arranged on the cabin door 20. Alternatively, the lock shaft portion 203002 is arranged on the cabin body 10, and the lock body portion 203001 is arranged on the cabin door 20. The door lock structure 2030 is electrically connected to the controller, which regulates the connection or disconnection of the lock body portion 203001 and the lock shaft portion 203002.

Furthermore, as shown in FIGS. 3 and 4, the door lock structure 2030 includes a lock body portion 203001 and a lock shaft portion 203002. The lock body portion 203001 includes a fixed part 203003 and a slider 203004 that is slidably connected to the fixed part 203003. The slider 203004 includes a first support 203005 and an electromagnet 203006 fixed on the first support 203005. The slider 203004 further includes a connecting plate 203007, which includes a bent hook portion 203008 and a suction plate portion 203009. The connecting plate 203007 can be relatively rotatably connected to the first support 203005, to enable the suction plate portion 203009 to move in a direction close to or away from the electromagnet 203006. The bent hook portion 203008 has a first receiving slot for receiving the lock shaft portion 203002 when the door lock structure 2030 is locked. The lock body portion 203001 is arranged on the cabin body 10, and the lock shaft portion 203002 is arranged on the cabin door 20. Alternatively, the lock shaft portion 203002 is arranged on the cabin body 10, and the lock body portion 203001 is arranged on the cabin door 20. The controller is electrically connected to the electromagnet 203006, and is configured to control the power on or off of the electromagnet 203006.

Specifically, when the cabin door 20 moves close to the cabin body 10, the connecting plate 203007 is subjected to an external force and rotates relative to the first support 203005, causing the lock shaft portion 203002 to be placed in the first receiving slot. The controller controls the electromagnet 203006 to be energized, causing the electromagnet 203006 to be connected to the suction plate portion 203009 through attraction, and the connecting plate 203007 to be fixed relative to the first support 203005, and the lock body portion 203001 to be fixedly connected to the lock shaft portion 203002. At the same time, the controller controls the slider 203004 to slide relative to the fixed part 203003, thereby driving the cabin door 20 to move further closer to the cabin body 10 until the cabin door 20 is tightly connected to the cabin body 10. When it is necessary to reopen the cabin door 20, the controller controls the electromagnet 203006 to power off, and the connecting plate 203007 can rotate relative to the first support 203005, causing the lock shaft portion 203002 to detach from the first receiving slot, achieving the opening of the cabin door 20. The cryogenic physical therapy cabin 1 adopts a door lock structure 2030 to connect the cabin door 20 and the cabin body 10. The opening or closing of the door lock structure 2030 can be controlled by the controller. Therefore, in the case of a unmanned cryogenic physical therapy cabin 1, the controller can control the connection or disconnection of the lock body portion 203001 and the lock shaft portion 203002 based on the internal situation of the cryogenic physical therapy cabin 1, thereby controlling the opening or closing of the cabin door 20, reducing the probability that users inside the cryogenic physical therapy cabin 1 are unable to leave for a long time due to the failure of the cabin door 20 to open in time, which can improve the safety of the cryogenic physical therapy cabin 1 during use.

Furthermore, as shown in FIGS. 3 and 4, the fixed part 203003 includes a first mounting plate 203011 and a first side plate 203012 fixedly connected to the first mounting plate 203011. The first mounting plate 203011 is configured for fixedly connecting to the cabin body 10 or the cabin door 20. The first side plate 203012 is provided with a first guide rail 203013, and the extension direction of the first guide rail 203013 is perpendicular to that of the first mounting plate 203011. The slider 203004 further includes at least one first pulley 203014, which is arranged on the first support 203005 and is slidably connected to the first guide rail 203013.

Specifically, as shown in FIGS. 3 and 4, the fixed part 203003 can be fixed on the cabin door 20 or the cabin body 10 through the first mounting plate 203011. The first guide rail 203013 cooperates with the first pulley 203014 to slide the slider 203004 along the extension direction of the first guide rail 203013, providing guidance for the sliding of the slider 203004. Driven by the first pulley 203014, the slider 203004 slides on the fixed part 203003, further locking the cabin body 10 and the cabin door 20.

Furthermore, as shown in FIGS. 3 and 4, the fixed part 203003 further includes a second side plate 203015, which is connected to the first mounting plate 203011 and is arranged parallel to the first side plate 203012, and on which a second guide rail 203016 is provided. The slider 203004 further includes at least one second pulley 203017, which is arranged on the first support 203005 and is slidably connected to the second guide rail 203016.

Furthermore, as shown in FIGS. 3 and 4, the first guide rail 203013 and the second guide rail 203016 form a dual guide rail structure, reducing the probability of derailment of the slider 203004 during the sliding process on the fixed part 203003, increasing the sliding stability of the slider 203004, and thereby enhancing the stability of the door lock structure 2030. The first mounting plate 203011, the first side plate 203012, and the second side plate 203015 can jointly form a receiving space, within which some structures of the slider 203004 can slide back and forth along the extension direction of the guide rail.

Furthermore, as shown in FIGS. 3 and 4, the cryogenic physical therapy cabin further includes a driving mechanism 2040, which includes a gear 204001 and a gear rack 204002. The gear 204001 is arranged on the fixed part 203003, the gear rack 204002 is arranged on the first support 203005, and the gear 204001 is meshed with the gear rack 204002. Alternatively, the gear 204001 is arranged on the first support 203005, and the gear rack 204002 is arranged on the fixed part 203003. The driving mechanism 2040 further includes an electric motor 204003 connected to the gear 204001.

Specifically, the electric motor 204003 provides power to drive the gear 204001 to rotate. The meshing transmission between the gear 204001 and the gear rack 204002 can enable the gear rack 204002 to drive the slider 203004 to move in a straight line, making the door lock structure 2030 more compact in structure and enhancing the reliability of the operation process of the door lock structure 2030. A second mounting plate 203018 is installed between the first side plate 203012 and the second side plate 203015, and the gear 204001 is installed on the second mounting plate 203018. The electric motor 204003 can be a stepper electric motor 204003, which is installed on a side of the second mounting plate 203018 away from the gear 204001.

Furthermore, as shown in FIGS. 3 and 4, the slider 203004 further includes a first elastic element 203019, one end of which is fixedly connected to the first support 203005 and the other end of which is fixedly connected to the suction plate portion 203009.

In the embodiment of the present application, the first elastic element 203019 is connected to the first support 203005 and the suction plate portion 203009, which can limit the rotation angle of the connecting plate 203007, and also can reset the connecting plate 203007 through its own rebound force after the lock shaft portion 203002 drives the connecting plate 203007 to rotate, thereby smoothly connecting or disconnecting the lock shaft portion 203002 and the locking body portion 203001. The first elastic element 203019 can include a spring, an elastic strip, etc.

Furthermore, as shown in FIG. 1, the cabin body 10 further includes a limit switch 104002, which is configured to detect the distance between the cabin door 20 and the cabin body 10.

When the user or the door closer 2010 drives the cabin door 20 close to the cabin body 10 to within the sensing range of the limit switch 104002, the limit switch 104002 closes to energize the electromagnet 203006, thus connecting the lock body portion 203001 and the lock shaft portion 203002, and the lock structure 2030 is in a locked state. Limit switch 104002 can timely detect the closed state of the cabin door 20, improving the intelligence of the door lock structure 2030 and the cryogenic physical therapy cabin 1.

In some embodiments of the present application, as shown in FIG. 1, the cryogenic physical therapy cabin 1 further includes a human body sensor 104003 and a timer, which are electrically connected to the controller. The human body sensor 104003 is arranged in the sauna room, and the controller is further configured to control the timer on or off according to the sensing result of the human body sensor 104003. The human body sensor 104003 can timely detect the situation of the user inside cabin body 10, improving the intelligence of the cryogenic physical therapy cabin 1.

In this embodiment, the human body sensor 104003 is configured to detect whether there is anyone in the sauna room. When the controller determines that a user has entered the sauna room based on the detection results of the human body sensor 104003, the controller starts the timer to start timing. On the contrary, when the controller determines that the user has left the sauna room based on the detection results of the human body sensor 104003, the controller controls the timer to stop timing.

In some embodiments of the present application, the controller is further configured to control the operation states of the air outlet module and the refrigeration module based on the timing duration of the timer. When the timing duration of the timer exceeds a second preset time or a user's preset physical therapy time, the controller can control the air outlet module and refrigeration module to turn off, further improving the intelligence and safety performance of the cryogenic physical therapy cabin 1, wherein, the second preset duration can be the maximum duration for which the user will not be in danger while in the sauna room.

Furthermore, the controller is further configured to control the connection or disconnection of the lock body portion 203001 and the lock shaft portion 203002 based on the timing duration of the controller. By combining the timer, the door lock structure 2030, and the controller, the intelligence and safety performance of the cryogenic physical therapy cabin 1 have been further improved.

In this embodiment, the timing duration of the timer is determined according to the user adjustment instruction or the second preset duration stored in the controller. After the timing duration of the timer exceeds the second preset duration or the user's preset physical therapy time, the controller controls to disconnect the electrical supply to the electromagnet 203006, disconnects the lock body portion 203001 and the lock shaft portion 203002, and the door lock structure 2030 is in an unlocked state. The user can push and open the cabin door 20 to leave the cryogenic physical therapy cabin 1, which can reduce the probability of danger due to that the user forgets the usage time and can further improve the safety of the cryogenic physical therapy cabin during use.

Furthermore, the controller can restart the timer after a new user enters the cryogenic physical therapy cabin, and repeat the action of controlling to disconnect the electrical supply to the electromagnet 203006 when the user's usage time reaches the second preset time or the user's preset physical therapy time.

In some embodiments of the present application, the cryogenic physical therapy cabin 1 further includes an alarm, which is electrically connected to the controller. The controller is further configured to control the alarm to provide an alarm when the timing duration exceeds the preset alarm duration. The controller adjusts the alarm to send an alarm signal to remind the duty personnel, wherein the alarm signal can be sound, light, etc. Through the joint action of the alarm and the controller, the alarm can send an alarm signal to prompt the duty personnel to handle it in a timely manner, reducing the probability of frostbite of users and improving the safety performance of the cryogenic physical therapy cabin 1.

In this embodiment, when the timing duration of the timer reaches a preset alarm duration and the human body sensor 104003 detects that the user in the sauna room has not left the sauna room, the controller can also determine whether the timing duration exceeds the preset alarm duration based on the detection results of the human body sensor 104003. After the timing duration exceeds the preset alarm duration, the controller is further configured to adjust the operation states of the air outlet module, the refrigeration module, and the first heater 1030. The controller adjusts the refrigeration module to stop cooling, the controller adjusts the air outlet module to stop the rotation of the fan 102002, and the controller activates the first heater 1030 to start heating, so that the sauna room is recovered to a room temperature, which reduces the probability of danger due to that the user is in a low temperature environment for a long time, and improves safety.

In other implementations, alarm signals can also be output through terminals such as mobile phones and computers that establish communication connections with the main control module. The specific process will not be repeated here.

Figure 5:
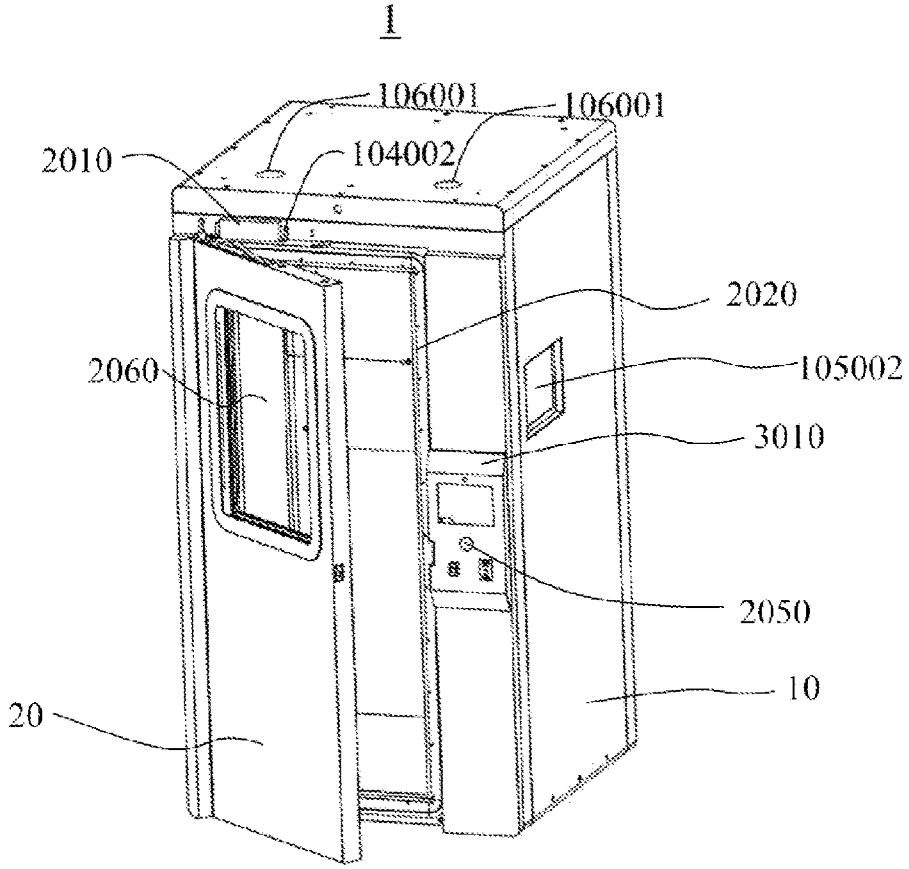
FIG. 5 is another schematic structural diagram of the cryogenic physical therapy cabin provided in the embodiments of the application.

In some embodiments of the present application, as shown in FIGS. 1 and 5, the cryogenic physical therapy cabin 1 further includes an emergency switch 2050, which is configured to convert the lock body portion 203001 and lock shaft portion 203002 from a connected state to a disconnected state. By providing the emergency switch 2050, it is beneficial to improve the safety performance of the cryogenic physical therapy cabin 1.

In this embodiment, as shown in FIGS. 3 and 4, the emergency switch 2050 further includes a connector 205001, an eccentric wheel 205002, and a microswitch 205003. The emergency switch 2050 is connected to one end of the connector 205001, the other end of the connector 205001 is connected to the eccentric wheel 205002, the eccentric wheel 205002 is rotatably connected to the electromagnet 203006, the microswitch 205003 is fixed on the eccentric wheel 205002, and the microswitch 205003 is electrically connected to the electromagnet 203006. Under the action of an external force, the emergency switch 2050 drives the connector 205001 to move, which in turn drives the eccentric wheel 205002 to rotate. The eccentric wheel 205002 triggers the microswitch 205003, which in turn causes the electromagnet 203006 to power off and unlocks the door lock structure 2030. The connector 205001 can be a steel wire or a steel rod.

Furthermore, the emergency switch 2050 includes an internal emergency switch. The internal emergency switch is arranged inside the cabin body 10, and is connected to connector 205001. During use, if the user feels unwell in the cryogenic physical therapy cabin 1, he/she can unlock the door lock structure 2030 by pressing the internal emergency switch, and then push and open the cabin door 20 to leave the sauna room, ending the physical therapy.

Furthermore, the emergency switch 2050 further includes an external emergency switch. The external emergency switch is installed outside the cabin body 10, and is connected to the connector 205001. In other implementations, the external emergency switch is electrically connected to the controller. After the controller detects the activation of the external emergency switch, the controller controls the door lock structure 2030 to unlock. After the user's physical therapy time in the cryogenic physical therapy cabin 1 exceeds the preset alarm time, the alarm will send an alarm signal. After receiving the alarm signal, the duty personnel can press the external emergency switch to open cabin door 20 to rescue the user.

Figure 6:
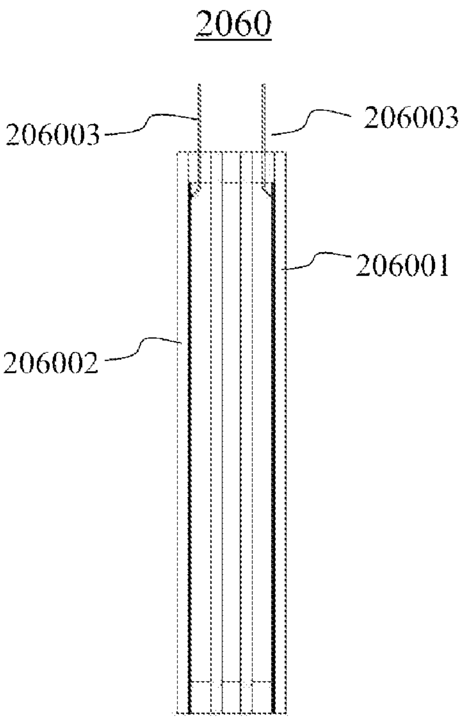
FIG. 6 is a schematic structural diagram of a glass window structure provided in the embodiments of the application.

In some embodiments of the present application, as shown in FIGS. 5 and 6, the cabin door 20 further includes a glass window structure 2060, which is arranged on the cabin door 20. The glass window structure 2060 includes at least two pieces of glass fixedly connected and arranged in parallel with each other, and there is an air gap between the adjacent two pieces of glass. An electric heater is arranged on the first glass 206001 in the at least two pieces of glass close to the sauna room. The controller is electrically connected to the electric heater, and is configured to control the operation state of the electric heater.

During the use of the cryogenic physical therapy cabin 1, the electric heater is energized to heat the glass window structure 2060. The temperature of the first glass 206001 connected to the sauna room is higher than that of the sauna room, and preferably, the temperature of the first glass 206001 is 10 to 20° C. higher than that of the sauna room. Moreover, maintaining the temperature of the first glass 206001 within a certain range can effectively improve the frosting or fogging of the glass window structure 2060, reduce the obstruction of frost layers and other factors to the glass window structure 2060, and enable duty personnel to observe the internal situation of the cryogenic physical therapy cabin 1 in real-time through the glass window structure 2060, thereby improving the safety performance of the cryogenic physical therapy cabin 1.

Furthermore, a piece of second glass 206002 further from the sauna room in the at least two pieces of glass is equipped with an electric heater. Providing an electric heater on the second glass 206002 is beneficial for reducing the probability of mist or dew appearing on the surface of the second glass 206002. In addition, the electric heater can also generate heat when dew is already formed on the second glass 206002, thereby quickly evaporating the dew on the glass window structure 2060 and reducing the obstruction of dew and other objects to the glass window structure 2060, so as to enable duty personnel to observe the internal situation of the cryogenic physical therapy cabin 1 in real-time through the glass window structure 2060, further improving the safety performance of the cryogenic physical therapy cabin 1.

Furthermore, the electric heater includes a heating coating arranged on at least one side surface of the first glass 206001, and the electric heater further includes an electric conductor 206003, which is electrically connected to the heating coating and is electrically connected to the controller. The heating coating can include a semiconductor coating, etc. The controller controls the energizing and the heating of the heating coating by energizing the electric conductor 206003. The electric conductor 206003 is located between two pieces of glass, so that the overall visible area of the first glass 206001 will not be reduced due to the obstruction of the electric conductor 206003, resulting in a relatively better light transmission performance of the first glass 206001.

Furthermore, the electric heater includes a heating wire arranged on the first glass 206001, which is electrically connected to the controller. The heating wire has less obstruction to the glass window structure 2060, which can reduce the impact on the transparency of the glass window structure 2060. In addition, the heating wires are evenly distributed on the first glass 206001, which has the advantage of uniform heating.

Furthermore, the glass window structure 2060 includes four pieces of glass fixedly connected and arranged parallel to each other. Four pieces of glass are installed in the glass window structure 2060, and multi-layer glass can improve the airtightness and thermal insulation performance of the glass window structure 2060.

Furthermore, the adjacent two pieces of glass are connected by bonding. In the glass window structure 2060, a bonding layer can be provided between adjacent two pieces of glass. The adjacent two pieces of glass are connected by bonding, which has high stability and low complexity, and low production cost. In addition, the adhesive layer has good thermal insulation performance, which can further improve the thermal insulation effect of the glass window structure 2060, and thus further improve the thermal insulation performance of the cryogenic physical therapy cabin 1.

In some embodiments of the present application, as shown in FIG. 1, the cryogenic physical therapy cabin 1 further includes an intercom system 105001, a display screen 105002, and a camera 105003. The intercom system 105001 includes a first intercom terminal located inside the cabin body 10 and a second intercom terminal located outside the cabin body 10. The display side of the display screen 105002 is located inside the cabin body 10, and the camera 105003 is located inside the cabin body 10.

The camera 105003 is used for real-time monitoring of the situation inside the sauna room, the intercom system 105001 is used for users entering the sauna room to communicate with duty personnel, and the display screen 105002 is configured to play safety prompts to users. Users who enter the cryogenic physical therapy cabin 1 for physical therapy can provide feedback to the duty personnel through the intercom system 105001 at any time during use when encountering emergency situations. The duty personnel can also handle sudden situations inside the sauna room in a timely manner through the surveillance video of the camera 105003, which is beneficial for improving the safety performance of the cryogenic physical therapy cabin 1.

In other implementation, as shown in FIG. 1, emergency components, such as emergency cotton clothes, emergency glass hammers 105004, are further equipped inside the cabin body 10. When the door lock structure 2030 cannot be opened, the emergency cotton clothes are used for user warmth, and the emergency glass hammer 105004 is used for users to break and escape from a window.

In some embodiments of the present application, as shown in FIG. 5, the cryogenic physical therapy cabin 1 further includes a main control operation panel 3010, which is arranged on the outer wall of the cabin body 10. The main control operation panel 3010 is electrically connected to the controller, and is configured to receive the user adjustment instruction and send it to the controller. By providing the main control operation panel 3010 in the cryogenic physical therapy cabin 1, it is convenient for users to input the user adjustment instruction, which is conducive to improving the intelligence level of the cryogenic physical therapy cabin 1.

In this embodiment, the main control operation panel 3010 is integrated with a physical switch, a button, a touchpad, etc., as an input component for the user adjustment instruction. Optionally, the main control operation panel 3010 is also equipped with display components that can be configured to display operating parameters such as the temperature inside the cabin body 10, the wind speed of the air outlet module, and the cooling capacity of the refrigeration module, facilitating real-time monitoring of the operation state of the cryogenic physical therapy cabin 1 by the duty personnel.

In some embodiments of the present application, the main control operation panel 3010 includes a central control module, a data acquisition module, a communication module, and a storage module, and the main control operation panel is electrically connected to the controller. When users first use the cryogenic physical therapy cabin 1, they can store user information in the cryogenic physical therapy cabin 1 by operating the main control operation panel 3010. Afterwards, the cryogenic physical therapy cabin 1 can call the stored user information and adjust the cryogenic physical therapy cabin 1 into a user-desired operation state according to the user information, avoiding the need for users to repeatedly input user information before each therapy, improving the intelligence level of the cryogenic physical therapy cabin 1.

In this embodiment, the central control module, the data acquisition module, the communication module, and the storage module are electrically connected and integrated with the main control operation panel 3010. The central control module, the data acquisition module, the communication module, and the storage module communicate with each other. The storage module is configured to store computer programs, and the central control module is configured to execute programs stored on the storage module. Specifically, the data acquisition module obtains user information and sends it to the central control module. The central control module receives user information, converts to-be-processed data into the user adjustment instruction based on the user information, and sends the user adjustment instruction to the controller. The controller controls and adjusts the operation states of the air outlet module and the refrigeration module based on the received the user adjustment instruction.

The user information includes user physical therapy needs, user accounts, user fingerprints, user face images, etc. User information can be obtained through the data acquisition module, which includes a fingerprint collector, a face recognition camera, and an input component integrated in the main control operation panel 3010. The main control operation panel 3010 is communicated with the display screen 105002 through signals. The main control operation panel 3010 and the display screen 105002 can also be configured to display information including user accounts, physical therapy temperatures, physical therapy wind speeds, physical therapy time, etc.

Optionally, the main control operation panel 3010 can be configured to receive the user adjustment instruction input through mobile phones, remote controllers, and the like that establish communication connections with the main control operation panel 3010, thereby enabling the interaction between the cryogenic physical therapy cabin 1 and external terminals. Users can use external terminals to control the temperature and wind speed inside the sauna room, improving the convenience of operation.

Figure 7:
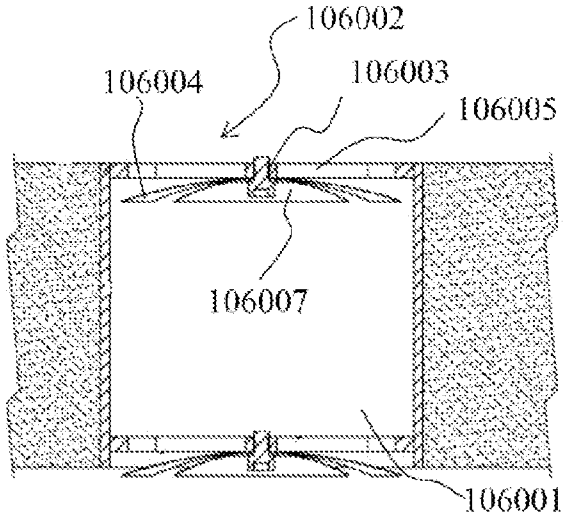
FIG. 7 is a cross-sectional view illustrating the assembly of an air pressure balance valve and an air pressure balance hole provided in the embodiments of the application.

In some embodiments of the present application, as shown in FIGS. 5 and 7, at least one air pressure balance hole 106001 is provided in the cabin body 10, and connects the interior and exterior of the cabin body 10. At least one air pressure balance valve 106002 is arranged in each air pressure balance hole 106001, and includes a second support 106003 and an elastic sheet 106004. The second support 106003 is abutted against the hole wall of the air pressure balance hole 106001, and at least one through hole 106005 is provided in the second support 106003. The elastic sheet 106004 is connected to the second support 106003, and along the axis direction of the air pressure balance hole 106001, the elastic sheet 106004 covers at least one through hole 106005, and elastic sheet 106004 is movable in a direction close to or away from the second support 106003. By providing the air pressure balance valve 106002, the air pressure inside the cryogenic physical therapy cabin 1 can be adjusted to maintain the air pressure the cryogenic physical therapy cabin 1 within a safe range.

In this embodiment, as preferred, the elastic sheet 106004 is made of metal material. During the process of a user entering the sauna room of the cryogenic physical therapy cabin 1, a large amount of warm air will be brought in when the cabin door 20 is opened. After the cabin door 20 is closed, the warm air is rapidly cooled by the cold air inside the sauna room, causing a decrease in the air pressure inside the sauna room. The pressures inside and outside cabin body 10 creates a pressure difference, and the external air pushes the elastic sheet 106004 to deform and enters the cabin. When the air pressures inside and outside the cabin body 10 are balanced, the elastic sheet 106004 utilizes its own elasticity to return to its original state, forming a hollow space to provide an insulation function.

Figure 8:
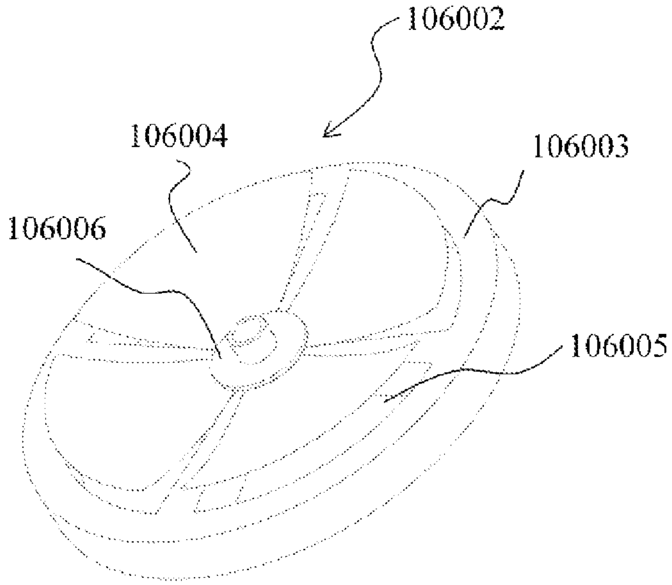
FIG. 8 is a schematic structural diagram of the air pressure balance valve provided in the embodiments of the present application.

Furthermore, as shown in FIGS. 7 and 8, the elastic sheet 106004 includes a first portion and a second portion. The first portion is fixedly connected to the second support 106003 and covers at least one through hole 106005 along the axis direction of the air pressure balance hole 106001. The second portion can move in a direction close to or away from the second support 106003. Preferably, there are four elastic sheets 106004, and there are correspondingly four through holes 106005. During the process of external air entering the sauna room, the first portion remains fixed to the second support 106003, and the second portion moves towards the side away from the second support 106003 under the action of air pressure, preventing the elastic sheet 106004 from rotating along the axis direction of the air pressure balance hole 106001, which otherwise causes the second portion to leak out of the opening position of the through hole 106005, causes cold air inside the cabin body 10 to leak into the external space, reduces the refrigeration performance of the cryogenic physical therapy cabin 1.

Furthermore, as shown in FIGS. 7 and 8, the air pressure balance valve 106002 further includes a pressing sheet 106006, which is fixedly arranged on the side of the elastic sheet 106004 away from the second support 106003, and the pressing sheet 106006 is in contact with the first portion. Providing the pressing sheet 106006 is beneficial for increasing the contact area between the first portion and the second support 106003, and improving the fixation effect between the first portion and the second support 106003.

Furthermore, as shown in FIG. 7, the air pressure balance valve 106002 further includes a bracket 106007, which is abutted against the elastic sheet 106004. The bracket 106007 is located on the side of the elastic sheet 106004 away from the second support 106003. Along the axis direction of the air pressure balance hole 106001, the orthographic projection of the bracket 106007 covers the orthographic projection of the first portion, and the orthographic projection of the bracket 106007 at least partially covers the orthographic projection of the second portion. The bracket 106007 has a limiting effect on the displacement of the second portion towards the side away from the second support 106003, preventing the second portion from failing to be restored to its original state due to significant elastic deformation caused by the movement of the second portion, further improving the service life of the pneumatic balance valve 106002.

Furthermore, the air pressure balance valve 106002 further includes a second elastic element, which is arranged between the second support 106003 and the elastic sheet 106004, and through which the elastic sheet 106004 moves in a direction close to or away from the second support 106003. The second elastic element can be a spring. Providing the second elastic element is beneficial for buffering the movement of the elastic sheet 106004 under the action of air pressure, thereby reducing the deformation of the elastic sheet 106004 and further improving the service life of the air pressure balance valve 106002.

In some embodiments of the present application, the refrigeration module includes a compressor refrigeration structure or a liquid nitrogen refrigeration structure. By installing a compressor refrigeration structure or a liquid nitrogen refrigeration structure as well as an evaporator 1010 in the cryogenic physical therapy cabin 1, it is possible to continuously provide extremely low physical therapy temperatures for the sauna room with good insulation performance, which is conducive to improving the refrigeration effect and further improving the user's physical therapy effect.

In this embodiment, when the refrigeration module adopts a compressor refrigeration structure, the compressor refrigeration structure specifically includes a two-stage cascade refrigeration machine, a three-stage cascade refrigeration machine, a single machine automatic cascade refrigeration machine, or a single machine pre-cooling and automatic cascade refrigeration machine. The selection of compressor refrigeration structure is related to the number of sauna rooms. The specific structure can refer to the refrigeration structure of compressors in existing technologies, and will not be repeated here.

When the refrigeration module adopts a liquid nitrogen refrigeration structure, the refrigeration module is equipped with an evaporator 1010, a liquid nitrogen tank, a liquid nitrogen pipeline, and a flow valve. The evaporator 1010 is connected to the liquid nitrogen tank through the liquid nitrogen pipeline, and the evaporator 1010 is provided on the inner wall of the cabin body 10. The liquid nitrogen tank is provided on the outer wall of the cabin body 10, and the air in the sauna room is cooled by the vaporization and heat absorption of liquid nitrogen in the evaporator 1010. The flow valve is electrically connected to the controller, which controls the flow rate of the flow valve and thus controls the internal temperature of the sauna room. The liquid nitrogen refrigeration structure can reduce the internal temperature of the sauna room to −60° C. to −190° C.

In some embodiments of the present application, the cryogenic physical therapy cabin 1 further includes a second heater and a water receiving tray, which is located below the evaporator 1010 to receive defrosted water generated by the evaporator 1010. The second heater is located on the water receiving tray, and is electrically connected to the controller. In this embodiment, the second heater is controlled by the controller to start or stop heating, and the second heater is configured to prevent the defrosted water stored in the water receiving tray from condensing, facilitating the export of the defrosted water to the outside of the cryogenic physical therapy cabin 1.

By providing a second heater and a water receiving tray in the cryogenic physical therapy cabin 1, it is possible to prevent defrosted water from falling onto the ground in the sauna room and forming ice, preventing users from slipping and falling during use, and improving the safety performance of the cryogenic physical therapy cabin 1.

In some embodiments of the present application, as shown in FIG. 1, the cabin body 10 further includes a cover plate 102003 connected to the inner wall of the cabin body 10, and an air duct is formed between the cover plate 102003 and the inner wall. The evaporator 1010 is arranged at a first end of the air duct, and the fan blades 102001 are arranged at a second end of the air duct. The cover plate 102003 includes an air outlet 102004 connected to the second end, and a return air inlet 102005 connected to the first end.

In this embodiment, the air duct and the evaporator 1010 are located in the same vertical plane. The fan 102002 drives the fan blades 102001 to rotate, forming a low air pressure at the second end of the air duct. A pressure difference is formed between the first end of the air duct and the second end of the air duct, and the air inside the air duct flows from the first end of the air duct to the second end of the air duct due to the pressure difference. Then, the air inside the sauna room continuously enters from the return air inlet 102005, and undergoes heat exchange with the surface of the evaporator 1010 and cools down, The cooled air flows through the second end of the air duct and is exported from the air outlet 102004 to the sauna room.

The combined action of the air duct and the rotating fan blades 102001 causes forced convection between the cold air in the evaporator area and the cold air in the cabin body 10, increasing the heat exchange rate and thus improving the refrigeration performance of the cryogenic physical therapy cabin 1.

In some embodiments of the present application, the cryogenic physical therapy cabin 1 further includes a second temperature sensor, which is configured to collect a second temperature value at the cabin door 20. The air outlet module further includes an air outlet adjustment mechanism for adjusting the opening degree of the air outlet 102004, which is located at the air outlet 102004. The second temperature sensor, the air outlet adjustment mechanism are electrically connected to the controller, and the second temperature sensor is configured to send the detected second temperature value to the controller. The controller is further configured to adjust the operation state of the air outlet adjustment mechanism based on the second temperature value and the user adjustment instruction. In this embodiment, the second temperature sensor can be installed on the cabin door 20 or close to the cabin door 20.

By providing a second temperature sensor close to cabin door 20, it is advantageous to accurately collect the air temperature close to cabin door 20, which in turn facilitates the controller to adjust the air outlet adjustment mechanisms at different positions according to the actual temperature, providing different air volumes for different air outlets, improving the accuracy of adjustment and further energy-saving for the cryogenic physical therapy cabin 1.

Optionally, the air outlet adjustment mechanism can be composed of a driving device and a baffle, and the output end of the driving device is connected to one end of the baffle to drive the baffle to rotate relative to the air outlet 102004, thereby controlling the area covered by the baffle relative to the air outlet 102004, and achieving the adjustment of the opening degree of the air outlet 102004.

Furthermore, the cover plate 102003 further includes a cover plate extension located along the upper portion of the cabin body 10 and close to the cabin door 20. The cover plate extension and the inner wall of the cabin body 10 form an extension air duct, and multiple air outlets are provided along the extension direction of the extension air duct. The cryogenic physical therapy cabin 1 can also include multiple second temperature sensors and multiple air outlet adjustment mechanisms. The multiple air outlet adjustment mechanisms are respectively provided at the multiple air outlets, and the multiple second temperature sensors are provided in one-to-one correspondences with the multiple air outlets. The controller can adjust the opening degree of the multiple air outlets.

The controller is further configured to: after determining the first opening degree of each air outlet according to the preset apparent temperature and adjusting the air outlet adjustment mechanism according to the first opening degree, determine the actual apparent temperature according to the second temperature value corresponding to each air outlet and the first opening degree of each air outlet; if the actual apparent temperature is greater than the preset apparent temperature, determine the second opening degree of each air outlet according to the difference value between the actual apparent temperature and the preset apparent temperature, and adjust the air outlet adjustment mechanism according to the second opening degree to reduce the actual apparent temperature to the preset apparent temperature.

In some embodiments of the present application, as shown in FIG. 1, the air outlet adjustment mechanism includes a wind guide plate 102006, and the controller is further configured to adjust the angle between the plane where the wind guide plate 102006 is located and the vertical direction according to the user adjustment instruction.

In this embodiment, the user adjustment instruction can include the user's height, and the angle between the plane where the wind guide plate 102006 is located and the vertical direction can be adjusted according to the user's height, thereby ensuring that the wind direction of the air outlet 102004 faces the main trunk of the user's body, in order to achieve better physical therapy effects.

The embodiment in the second aspect of this application provides a cryogenic physical therapy cabin system, which includes a mobile terminal and the cryogenic physical therapy cabin 1 in any embodiment in the first aspect mentioned above. The mobile terminal is communicated with the main control module of the cryogenic physical therapy cabin 1 through signals.

The mobile terminal includes but is not limited to a mobile phone, a tablet computer, an intelligent cabin, etc. People who use the mobile terminal is the user, who can send a user adjustment instruction through the mobile terminal to control the operation state of the cryogenic physical therapy cabin 1. According to the cryogenic physical therapy cabin system in the embodiment of the present application, it shares the same inventive concept as the cryogenic physical therapy cabin 1 in the embodiment in the first aspect mentioned above. Therefore, the cryogenic physical therapy cabin system in the embodiment of the present application can achieve all the beneficial effects of the cryogenic physical therapy cabin 1 in the embodiment of the first aspect mentioned above.

It should be noted that the relationship terms herein such as "first", "second", and the like are only used for distinguishing one entity or operation from another entity or operation, but do not necessarily require or imply that there is any actual relationship or order between these entities or operations. Moreover, the terms "include", "comprise" or any other variants thereof are intended to cover non-exclusive inclusions, so that processes, methods, articles or devices including a series of elements include not only those elements listed but also those not specifically listed or the elements intrinsic to these processes, methods, articles, or devices. Without further limitations, elements defined by the sentences "comprise(s) a." or "include(s) a." do not exclude that there are other identical elements in the processes, methods, articles, or devices which include these elements.

All the embodiments of the present application are described in corresponding ways, same or similar parts in each of the embodiments can be referred to one another, and the parts emphasized are differences to other embodiments.

The embodiments described above are merely preferred embodiments of the present application, and not intended to limit the scope of the present application. Any modifications, equivalents, improvements or the like within the spirit and principle of the application should be included in the scope of the application.

What is claimed is:

1. A cryogenic physical therapy cabin, comprising:

a cabin body;

a cabin door, which is hinged with the cabin body to form at least one sauna room;

a refrigeration module, which comprises an evaporator arranged on an inner wall of the cabin body;

an air outlet module, which is arranged on the cabin body and comprises fan blades and a fan electrically connected to the fan blades, wherein the fan is configured to drive the fan blades to rotate to generate a circulating airflow inside the sauna room; and a main control module, which comprises a controller electrically connected to the fan and the refrigeration module, wherein the controller is configured to receive a user adjustment instruction and adjust operation states of the air outlet module and the refrigeration module according to the user adjustment instruction, wherein, the cryogenic physical therapy cabin further comprises a first temperature sensor, which is arranged on the inner wall of the cabin body, wherein first temperature sensor is electrically connected to the controller, and is configured to send a detected first temperature value to the controller, wherein the controller is further configured to adjust a rotation speed of the fan according to the first temperature value and the user adjustment instruction, wherein, the user adjustment instruction comprises a preset target apparent temperature, and the controller being further configured to adjust the rotation speed of the fan according to the first temperature value and the user adjustment instruction, comprises:

the controller being further configured to obtain a current first rotation speed of the fan, and calculate a current actual apparent temperature according to the first rotation speed and the first temperature value, the controller being further configured to calculate a difference value between the actual apparent temperature and the target apparent temperature, and adjust the rotation speed of the fan to a second rotation speed according to the difference value, wherein, at least one air pressure balance hole is arranged in the cabin body, and connects an interior and an exterior of the cabin body, and wherein at least one air pressure balance valve is arranged in each of the at least one air pressure balance hole, and comprises a support and an elastic sheet, wherein the support is abutted against a hole wall of the air pressure balance hole, and at least one through hole is arranged in the support; the elastic sheet includes a first portion and a second portion, the first portion is fixedly connected to the support and the second portion covers the at least one through hole along an axis direction of the air pressure balance hole, the second portion moves in a direction close to or away from the support; the air pressure balance valve further includes a pressing sheet, which is fixedly arranged on a side of the elastic sheet away from the support, and the pressing sheet is in contact with the first portion; the air pressure balance valve further includes a bracket, which is abutted against the elastic sheet, the bracket is located on the side of the elastic sheet away from the support; along the axis direction of the air pressure balance hole, an orthographic projection of the bracket covers an orthographic projection of the first portion, and the orthographic projection of the bracket at least partially covers an orthographic projection of the second portion; the air pressure balance valve further includes a second elastic element, which is arranged between the support and the elastic sheet, and through which the elastic sheet moves in the direction close to or away from the support.

2. The cryogenic physical therapy cabin as claimed in claim 1, wherein, the cryogenic physical therapy cabin further comprises a first heater, which is arranged on the evaporator and is electrically connected to the controller, wherein the controller is further configured to adjust an operation state of the first heater.

3. The cryogenic physical therapy cabin as claimed in claim 1, wherein, the cabin body further comprises a cover plate connected to the inner wall of the cabin body, and an air duct is formed between the cover plate and the inner wall, wherein the evaporator is arranged at a first end of the air duct, and the fan blades are arranged at a second end of the air duct, and the cover plate comprises an air outlet connected to the second end, and a return air inlet connected to the first end.

4. The cryogenic physical therapy cabin as claimed in claim 1, wherein, the cryogenic physical therapy cabin further comprises a human body sensor and a timer, which are electrically connected to the controller, wherein the human body sensor is arranged in the sauna room, and the controller is further configured to control the timer on or off according to a sensing result of the human body sensor; and the controller is further configured to control the operation states of the air outlet module and the refrigeration module according to a timing duration of the timer.

5. The cryogenic physical therapy cabin as claimed in claim 1, wherein, the cabin door further comprises a glass window structure, which comprises at least two pieces of glass fixedly connected and arranged in parallel with each other, wherein there is an air gap between adjacent two pieces of glass, and an electric heater is arranged on a first glass in the at least two pieces of glass close to the sauna room; and the controller is electrically connected to the electric heater, and is configured to control an operation state of the electric heater.

6. The cryogenic physical therapy cabin as claimed in claim 1, wherein, the cryogenic physical therapy cabin further comprises a main control operation panel, which is arranged on an outer wall of the cabin body and is electrically connected to the controller, wherein the main control operation panel is configured to receive the user adjustment instruction and send the user adjustment instruction to the controller.

7. The cryogenic physical therapy cabin as claimed in claim 6, wherein, the main control operation panel comprises a central control module, a data acquisition module, a communication module, and a storage module, wherein the main control operation panel is electrically connected to the controller.

8. The cryogenic physical therapy cabin as claimed in claim 1, wherein, the refrigeration module comprises a compressor refrigeration structure or a liquid nitrogen refrigeration structure.

9. A cryogenic physical therapy cabin system, comprising a mobile terminal and the cryogenic physical therapy cabin as claimed in claim 1, wherein the mobile terminal is communicated with the main control module of the cryogenic physical therapy cabin through signals.

* * * * *